(12) United States Patent
Yoshitani et al.

(10) Patent No.: US 11,452,795 B2
(45) Date of Patent: *Sep. 27, 2022

(54) MEDICAL LUBRICATING MEMBER, MEDICAL DEVICE USING MEDICAL LUBRICATING MEMBER, AND METHOD OF PRODUCING MEDICAL LUBRICATING MEMBER

(71) Applicant: FUJIFILM Corporation, Tokyo (JP)

(72) Inventors: Toshihide Yoshitani, Kanagawa (JP); Nobuharu Takahashi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 504 days.

This patent is subject to a terminal disclaimer.

(21) Appl. No.: 16/506,454

(22) Filed: Jul. 9, 2019

(65) Prior Publication Data

US 2019/0328932 A1  Oct. 31, 2019

Related U.S. Application Data

(63) Continuation of application No. PCT/JP2017/047348, filed on Dec. 28, 2017.

(30) Foreign Application Priority Data

Jan. 13, 2017  (JP) .............................. JP2017-003842

(51) Int. Cl.
*A61L 27/34*  (2006.01)
*A61L 29/08*  (2006.01)
*A61L 29/14*  (2006.01)
*A61L 31/10*  (2006.01)
*A61M 16/04*  (2006.01)

(52) U.S. Cl.
CPC ............... *A61L 27/34* (2013.01); *A61L 29/08* (2013.01); *A61L 29/14* (2013.01); *A61L 31/10* (2013.01); *A61L 2400/10* (2013.01); *A61M 16/04* (2013.01)

(58) Field of Classification Search
CPC .......... A61L 27/34; A61L 29/08; A61L 29/14; A61L 31/10; A61L 2400/10; A61L 29/06;
(Continued)

(56) References Cited

U.S. PATENT DOCUMENTS 5,160,790 A    11/1992  Elton
2003/0198821 A1  10/2003  Terry et al.
(Continued)

FOREIGN PATENT DOCUMENTS

CN    104721875 A    6/2015
JP    11-255926 A    9/1999
(Continued)

OTHER PUBLICATIONS

Office Action dated Jun. 2, 2020 in Japanese Application No. 2018-561331.
(Continued)

*Primary Examiner* — Michael B Nelson
(74) *Attorney, Agent, or Firm* — Sughrue Mion, PLLC

(57) ABSTRACT

Provided are a medical lubricating member including a silicone base material, and a lubricating coated film which is laminated on at least one surface of the silicone base material, in which the silicone base material contains a reactive functional group in the surface on which the lubricating coated film is laminated, and the lubricating coated film is a film formed of a composition containing a hydrophilic polymer and polyisocyanate; a medical device using the medical lubricating member; and a method of producing the medical lubricating member.

15 Claims, 1 Drawing Sheet

(58) Field of Classification Search
CPC .... A61L 29/085; A61L 2420/08; A61M 16/04
See application file for complete search history.

(56) References Cited

U.S. PATENT DOCUMENTS

2008/0163870 A1      7/2008   Kusunoki et al.
2011/0086077 A1*     4/2011   McCrea .............. A61L 26/0019
                                                              424/445

FOREIGN PATENT DOCUMENTS

| JP | 2002-529170 A | 9/2002 |
| JP | 2006-102099 A | 4/2006 |
| JP | 2011-188908 A | 9/2011 |

OTHER PUBLICATIONS

Communication dated Feb. 23, 2022 by the European Patent Office in corresponding European Application No. 17891179.8.
Extended European Search Report dated Dec. 18, 2019 in corresponding European Application No. 17891179.8.
International Search Report dated Apr. 3, 2018 from the International Searching Authority in counterpart International Application No. PCT/JP2017/047348.
International Preliminary Report on Patentability dated Jun. 25, 2019 from the International Bureau in counterpart International Application No. PCT/JP2017/047348.
Written Opinion dated Apr. 3, 2018 from the International Bureau in counterpart International Application No. PCT/JP2017/047348.
Office Action dated Nov. 26, 2021 from the China National Intellectual Property Administration in corresponding CN Application No. 201780077514.9.
Communication dated Mar. 26, 2021, from The State Intellectual Property Office of the P.R. of China in Application No. 201780077514.9.
Communication dated Aug. 2, 2021 by the Chinese Patent Office in corresponding Chinese Application No. 201780077514.9.
Office Action dated May 10, 2022 issued by the Chinese Patent Office in corresponding Chinese Application No. 201780077514.9.

* cited by examiner

MEDICAL LUBRICATING MEMBER, MEDICAL DEVICE USING MEDICAL LUBRICATING MEMBER, AND METHOD OF PRODUCING MEDICAL LUBRICATING MEMBER

CROSS-REFERENCE TO RELATED APPLICATIONS

This application is a Continuation of PCT International Application No. PCT/JP2017/047348 filed on Dec. 28, 2017, which claims priority under 35 U.S.C. § 119 (a) to Japanese Patent Application No. 2017-003842 filed in Japan on Jan. 13, 2017. Each of the above applications is hereby expressly incorporated by reference, in its entirety, into the present application.

BACKGROUND OF THE INVENTION

1. Field of the Invention

The present invention relates to a medical lubricating member, a medical device using the medical lubricating member, and a method of producing the medical lubricating member.

2. Description of the Related Art

As a medical device to be inserted into the blood vessels, tracheas, gastrointestinal tracts, other body cavities, or tissues in order to examine or treat the human bodies, for example, JP2011-188908A describes a medical device which suppresses degradation of lubricity using a contrast agent contained in the outer peripheral surface of the medical device. In this medical device, a urethane-based polymer layer is provided on the outer peripheral surface of the medical device on which a resin layer containing the contrast agent is formed, and the outer peripheral surface of the urethane-based polymer layer is coated with a solution containing a maleic acid anhydride-based polymer and polyisocyanate so that a maleic acid anhydride-based polymer layer is laminated thereon. Further, JP2006-102099A describes a tracheotomy tube which is detachably attached to an incised part smoothly and in which phlegm or the like is unlikely to be accumulated therein. This tracheotomy tube includes a luminal body comprising a lumen for clearing the airway, and a coated film exhibiting the surface lubricity at the time of wetting is formed on each of the inner surface that forms the lumen for clearing the airway of this luminal body and the surface of the tracheotomy tube.

SUMMARY OF THE INVENTION

The invention described in JP2011-188908A relates to a medical instrument having improved slipperiness with respect to human tissues at the time of wetting. The invention described in JP2006-102099A relates to a medical device having improved slipperiness with respect to human tissues at the time of tracheostomy or the like, components to be generated from human bodies such as phlegm or the like, and food.

In a case where a medical device is used in contact with the human tissues and the friction between the medical device and the surface of the tissues is large, the tissues are damaged. For example, since an endoscope is used by sliding inside the body cavity, it is important to improve the slipperiness of a surface member of the endoscope to be brought into contact with the tissues inside the body cavity. Since the inside of the body cavity is in a wet state, the surface member of the medical device is required to have improved slipperiness particularly in a wet state.

Further, in a state in which a medical tube is inserted into the body cavity and water is allowed to pass through this tube, the inside of the body cavity is observed or a biopsy is performed by inserting a camera, a jig, or the like thereinto in some cases. In this form, the slipperiness between a jig and the inner wall of the tube in a wet state needs to be improved.

An object of the present invention is to provide a medical lubricating member in which the slipperiness is excellent in a wet state and degradation of the slipperiness due to repeated use is unlikely to occur. Further, another object of the present invention is to provide a medical device using the medical lubricating member. Further, still another object of the present invention is to provide a method of producing the medical lubricating member.

As the result of intensive examination conducted by the present inventors, it was found that the above-described objects can be achieved by a medical lubricating member in which a reactive functional group is introduced to at least one surface of a silicone base material or an adhesive layer containing a reactive functional group is laminated on at least one surface of a silicone base material, and the surface to which the reactive functional group has been introduced has a film formed of a composition containing a hydrophilic polymer or polyisocyanate, thereby completing the present invention based on this knowledge.

The above-described objects are achieved by the following means.

<1> A medical lubricating member comprising: a silicone base material; and a lubricating coated film which is laminated on at least one surface of the silicone base material, in which the silicone base material contains a reactive functional group in the surface on which the lubricating coated film is laminated, and the lubricating coated film is a film formed of a composition containing a hydrophilic polymer and polyisocyanate.

<2> A medical lubricating member comprising: a silicone base material; an adhesive layer which is provided on at least one surface of the silicone base material; and a lubricating coated film which is laminated on a surface of the adhesive layer opposite to a surface where the silicone base material is in contact, in which the adhesive layer contains a reactive functional group in the surface on which the lubricating coated film is laminated, and the lubricating coated film is a film formed of a composition containing a hydrophilic polymer and polyisocyanate.

<3> The medical lubricating member according to <1> or <2>, in which the silicone base material is a tubular silicone base material.

<4> The medical lubricating member according to <3>, in which the lubricating coated film is provided at least inside the tubular silicone base material.

<5> The medical lubricating member according to <1>, in which the reactive functional group is at least one of a hydroxyl group, a carboxy group, or an amino group.

<6> The medical lubricating member according to <2>, in which the reactive functional group is at least one of an amino group, an isocyanato group, a glycidyl group, a hydroxyl group, a carboxy group, a formyl group, an acid anhydride group, or an oxazoline ring.

<7> The medical lubricating member according to any one of <1> to <6>, in which the hydrophilic polymer is at least one of polyvinylpyrrolidone, a maleic acid anhydride copolymer, or hyaluronic acid.

<8> The medical lubricating member according to any one of <1> to <7>, in which the polyisocyanate is at least one of 1,6-hexamethylene diisocyanate, isophorone diisocyanate, 2,4-tolylene diisocyanate, 2,6-tolylene diisocyanate, m-xylylene diisocyanate, or 4,4'-diphenylmethane diisocyanate.

<9> The medical lubricating member according to any one of <1> to <8>, in which a ratio between a content of the hydrophilic polymer and a content of the polyisocyanate (hydrophilic polymer:polyisocyanate) in the film is 1:0.01 to 1 in terms of a mass ratio.

<10> The medical lubricating member according to any one of <1> to <9>, in which the medical lubricating member is a member for a medical device selected from a balloon, a connector, a rubber component for a medical device, an angiography tube, a tracheal tube, a feeding tube, a tube for a urinary system, an endoscope overtube, and a catheter.

<11> A medical device which uses the medical lubricating member according to any one of <1> to <9> and is selected from a balloon, a connector, a rubber component for a medical device, an angiography tube, a tracheal tube, a feeding tube, a tube for a urinary system, an endoscope overtube, and a catheter.

<12> A method of producing a medical lubricating member, comprising: a step of coating a silicone base material containing a reactive functional group in a surface thereof with a composition containing a hydrophilic polymer and polyisocyanate; and a step of heating the composition at 100° C. or higher.

<13> A method of producing a medical lubricating member, comprising: a step of coating an adhesive layer containing a reactive functional group in a surface thereof, which is disposed on a silicone base material, with a composition containing a hydrophilic polymer and polyisocyanate; and a step of heating the composition at 100° C. or higher.

In the present specification, the concept of "to" is used to indicate that the numerical values described before and after "to" are included as the lower limits and the upper limits.

In the present specification, in a case where a plurality of substituents, linking groups, or structural units (hereinafter, referred to as substituents or the like) are denoted by a specific reference or a plurality of substituents or the like are simultaneously or alternatively defined, the plurality of substituents or the like may be the same as or different from one another. The same applies to the definition of the number of substituents or the like. Further, in a case where a plurality of substituents or the like are close to one another (particularly adjacent to one another), this indicates that the substituents or the like may be linked or condensed to form a ring.

In the present specification, the terms "acrylic acid", "acrylamide", and "styrene" are used in a broader sense than usual.

In other words, the concept of "acrylic acid" includes all compounds having a structure of $R^A$—$C(=CR^B{}_2)COOH$ ($R^A$ and $R^B$ each independently represent a hydrogen atom or a substituent).

Further, the concept of "acrylamide" includes all compounds having a structure of $R^C$—$C(=CR^D{}_2)CONR^E{}_2$ ($R^C$, $R^D$, and $R^E$ each independently represent a hydrogen atom or a substituent).

Further, the concept of "styrene" includes all compounds having a structure of $R^F$—$C(=CR^G{}_2)C_6R^H{}_6$ ($R^F$, $R^G$, and $R^H$ each independently represent a hydrogen atom or a substituent).

In the present specification, in a case where the number of carbon atoms of a certain group is defined, the number of carbon atoms of this certain group indicates the number of carbon atoms of the whole group. In other words, in a case where this group further has a substituent, the number of carbon atoms thereof indicates the total number of carbon atoms including the number of carbon atoms in this substituent.

In the present invention, the "composition" indicates a mixture formed by uniformly mixing two or more components. Here, the uniformity may be substantially maintained or aggregation or uneven distribution may partially occur within the range where desired effects are exhibited, and a form in which two or more components are uniformly present is preferable.

In the present specification, the mass average molecular weight is a value (in terms of polystyrene) measured using gel permeation chromatography (GPC) unless otherwise specified.

The mass average molecular weight can be measured under a condition of a temperature of 23° C. and a flow rate of 1 mL/min specifically using a GPC device HLC-8220 (trade name, manufactured by Tosoh Corporation), N-methyl-2-pyrrolidone (manufactured by Wako Pure Chemical Industries, Ltd.) as an eluent, TSK-gel Super AWM-H (trade name, manufactured by Tosoh Corporation) as a column, and an RI detector.

The medical lubricating member or the medical device of the present invention has excellent slipperiness in a wet state and is capable of maintaining this slipperiness. Further, according to the method of producing the medical lubricating member of the present invention, it is possible to produce a medical lubricating member having the above-described excellent performance.

DESCRIPTION OF THE PREFERRED EMBODIMENTS

<Medical Lubricating Member>

A medical lubricating member according to a first embodiment of the present invention includes a silicone base material, and a lubricating coated film which is laminated on at least one surface of the silicone base material, in which the silicone base material contains a reactive functional group in the surface on which the lubricating coated film is laminated, and the lubricating coated film is a film formed of a composition containing a hydrophilic polymer and polyisocyanate. In other words, the lubricating coated film constitutes the outermost layer of the medical lubricating member.

Figure 1:
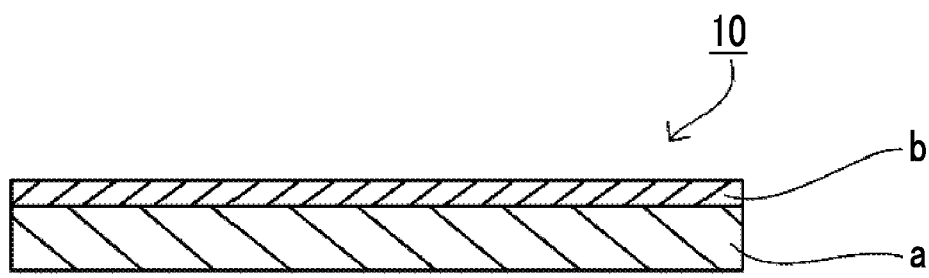
FIG. 1 is a cross-sectional view illustrating an embodiment of a medical lubricating member according to a first embodiment of the present invention.

A medical lubricating member 10 illustrated in FIG. 1 includes a silicone base material a, and a lubricating coated film b on one surface of the silicone base material a.

Further, a medical lubricating member according to a second embodiment of the present invention includes a silicone base material, an adhesive layer which is provided on at least one surface of the silicone base material, and a lubricating coated film which is laminated on a surface of the adhesive layer opposite to a surface where the silicone base material is in contact, in which the adhesive layer contains a reactive functional group in the surface on which the lubricating coated film is laminated, and the lubricating coated film is a film formed of a composition containing a hydrophilic polymer and polyisocyanate. In other words, the lubricating coated film constitutes the outermost layer of the medical lubricating member.

Figure 2:
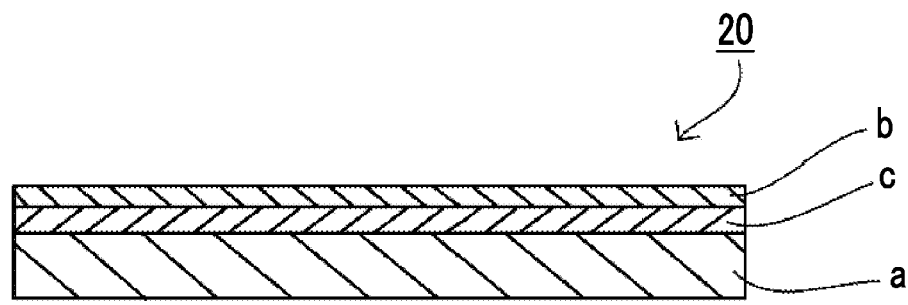
FIG. 2 is a cross-sectional view illustrating an embodiment of a medical lubricating member according to a second embodiment of the present invention.

A medical lubricating member 20 illustrated in FIG. 2 includes a silicone base material a, an adhesive layer c on one surface of the silicone base material a, and a lubricating coated film b on this adhesive layer c.

Hereinafter, the medical lubricating member is also simply referred to as a "member". Further, the silicone base material is also simply referred to as a "base material". Further, at least one surface of the silicone base material is also referred to as a "surface". Further, the film formed of the composition containing a hydrophilic polymer and polyisocyanate is also referred to as a "composition film". Further, both of the medical lubricating member according to the first embodiment of the present invention and the medical lubricating member according to the second embodiment of the present invention are also collectively referred to as a "medical lubricating member according to the embodiment of the present invention".

First, the medical lubricating member according to the first embodiment of the present invention will be described.

(Silicone Base Material)

The silicone may result from a reaction between first silane (for example, a first silicon-containing group such as a first alkoxysilyl group or a first hydroxysilyl group) and second silane (for example, a second silicon-containing group such as a second alkoxysilyl group or a second hydroxysilyl group).

The silicone base material indicates a base material containing polysiloxane in at least a surface thereof. The silicone base material used in the present invention is not particularly limited, and examples thereof include a base material formed of single silicone rubber or a single silicone resin and a base material whose surface is coated with any of these materials. As the member according to the embodiment of the present invention, silicone rubber is preferably used. The shape of the silicone base material is not particularly limited, and examples thereof include a sheet shape and a tube shape. Further, the thickness of the silicone base material is not particularly limited, but is preferably in a range of 10 to 50000 μm.

The silicone rubber is obtained by being cured using a curing agent for a silicone rubber composition. As this curing agent, a typical curing agent can be used. For example, in a case where the curing is carried out by a hydrosilylation reaction, a platinum group metal-based catalyst is used as a curing agent for a silicone rubber composition containing organohydrogen polysiloxane. In a case where peroxide crosslinking is carried out, a peroxide is used as a curing agent. Further, in a case where the silicone base material has a tube shape, a commercially available product may be used by being molded in a tube shape. Examples of the commercially available product include a silicone rubber sheet (trade name: KE-880-U, hardness of 80 A, manufactured by Shin-Etsu Chemical co., Ltd.).

Specific examples of the commercially available product include KE Series (manufactured by Shin-Etsu Chemical co., Ltd.), TSE Series (manufactured by Momentive Performance Materials Inc.), and ELASTSIL Series (manufactured by Wacker Asahikasei Silicone Co., Ltd.). These specific examples are described with the trade names thereof below.

KE Series (manufactured by Shin-Etsu Chemical co., Ltd.) KE931-U, KE941-U, KE951-U, KE961-U, KE971-U, KE981-U, KE961T-U, KE971T-U, KE871C-U, KE742-U, KE752-U, KE762-U, KE772-U, KE782-U, KE850-U, KE870-U, KE880-U, and KE890-U TSE Series (manufactured by Momentive Performance Materials Inc.)
TSE2267U, TSE2277U, TSE2287U, and TSE2297U
ELASTSIL Series (manufactured by Wacker Asahikasei Silicone Co., Ltd.)
EL1301, EL1401, EL1501, EL1601, EL1701, EL1801, EL4300, EL4406, EL4500, EL4610, EL4710, EL4810, EL3530, EL3630, EL3730, EL7101, EL7153, EL7210, and R401/10 to R401/90

Examples of the method of molding the silicone rubber or the silicone resin in a tube shape include press molding, extrusion molding blow molding, and injection molding.

In the member according to the first embodiment of the present invention, the lubricating coated film is laminated on at least one surface of the silicone base material, and the silicone base material contains a reactive functional group in the surface on which the lubricating coated film is laminated.

In the member according to the first embodiment of the present invention, since the reactive functional group forms a covalent bond or a hydrogen bond together with the hydrophilic polymer or polyisocyanate to be laminated, at least one of an amino group, a hydroxyl group, or a carboxy group is preferable, and a hydroxyl group or a carboxy group is more preferable as the reactive functional group.

A method of introducing the reactive functional group to the surface of the silicone base material is not particularly limited, and examples thereof include a physical surface treatment.

According to a method of performing the physical surface treatment, for example, the surface of the base material is irradiated with active energy rays, and a hydroxyl group (hydroxy group), a carboxy group, and/or an amino group (at least one group of a hydroxyl group, a carboxy group, or an amino group) is introduced to the surface of the base material. Examples of the active energy rays include α rays, γ rays, electron beams, X-rays, and ultraviolet rays. Further, a method of allowing the active species to act on the surface and similarly introducing a hydroxy group, a carboxy group, and/or an amino group (at least one group of a hydroxy group, a carboxy group, or an amino group) to the surface thereof is also used. Specific examples thereof include an oxygen plasma treatment, an atmospheric pressure plasma treatment, a corona treatment, a UV ozone treatment, and a treatment using ozone water. In the member according to the first embodiment of the present invention, an oxygen plasma treatment is preferable.

In addition, the method described in "Surface Treatment Handbook (ISBN: 978-4-900830-46-2 (4-900830-46-1), supervised by Hiroshi Mizumachi, first edition, 2000, NTS Inc.) is also exemplified as the method of performing a physical surface treatment.

The surface activation treatment may be performed in any of a non-oxidative atmosphere or an oxidative atmosphere. Examples of the non-oxidative atmosphere include an inert gas atmosphere such as nitrogen or argon, and a reducing gas atmosphere such as hydrogen. Examples of the oxidative atmosphere include an air atmosphere and an oxygen atmosphere.

(Lubricating Coated Film)

The lubricating coated film included in the member according to the first embodiment of the present invention is a film formed of a composition containing a hydrophilic polymer and polyisocyanate. In the member according to the first embodiment of the present invention, it is assumed that the polyisocyanate forms a unique network in addition to anchoring with respect to the silicone base material to form a structure in which the formed network is entangled with the network of the hydrophilic polymer so that a tough lubricating coated film is formed. Further, in the member according to the second embodiment invention described below, it is assumed that a tough lubricating coated film is formed similarly to the member according to the first embodiment by anchoring of the polyisocyanate with respect to the adhesive layer.

Hereinafter, the hydrophilic polymer and the polyisocyanate will be described.

—Hydrophilic Polymer—

The hydrophilic polymer used for the member according to the first embodiment of the present invention is not particularly limited. Here, the "hydrophilic polymer" indicates a polymer which is dissolved in water or swollen.

The mass average molecular weight of the hydrophilic polymer used in the member according to the first embodiment of the present invention is not particularly limited, but is preferably in a range of 1000 to 2000000, more preferably 10000 to 1500000, and still more preferably in a range of 100000 to 1000000. Further, it is preferable that the hydrophilic polymer used in the member according to the first embodiment of the present invention contains a reactive functional group.

Specific examples of the hydrophilic polymer used in the member according to the first embodiment of the present invention include hydrophilic polysaccharides such as hyaluronic acid, chondroitin sulfate, alginic acid, carrageenan, agarose, methyl cellulose, carboxymethyl cellulose, hydroxypropyl methyl cellulose, and oxidized cellulose; hydrophilic vinyl polymers such as polyvinylpyrrolidone, a maleic acid anhydride copolymer, polyacrylic acid, poly-N-vinylacetamide, an acrylamide copolymer, poly(2-(meth-acryloyloxy)ethylphosphoryl choline) (MPC polymer), N-(3-sulfopropyl)-N-(methacryloxyethyl)-N,N-dimethyl-ammonium betaine (SBMA polymer), and N-methacryloy-loxyethyl-N,N-dimethylammonium-α-N-methylcarboxy betaine (CBMA polymer); and copolymers of these. As the maleic acid anhydride copolymer, a copolymer of maleic acid anhydride and methyl vinyl ether, styrene, ethylene, vinyl acetate, and/or 1-hexene (at least one of methyl vinyl ether, styrene, ethylene, vinyl acetate, or 1-hexene) is preferable. In the member according to the embodiment of the present invention, the hydrophilic polymer may be used alone or in combination of two or more kinds thereof.

In the present invention, from the viewpoints of the hydrophilicity, the lubricity, and the biocompatibility of the polymer, at least one of polyvinylpyrrolidone, a maleic acid anhydride copolymer, or hyaluronic acid is preferable as the hydrophilic polymer.

—Polyisocyanate—

The polyisocyanate used in the member according to the first embodiment of the present invention is not particularly limited. Examples of the polyisocyanate include aliphatic, alicyclic, or aromatic polyisocyanate. Among examples thereof, tri- or higher valent polyisocyanate may be used or a low-molecular-weight compound or a high-molecular-weight compound may be used.

Specific examples of the polyisocyanate used in the member according to the first embodiment of the present invention include 1,6-hexamethylene diisocyanate, 2,4-tolylene diisocyanate, 2,6-tolylene diisocyanate, 4,4'-diphenylmethane diisocyanate, phenylene diisocyanate, m-xylylene diisocyanate, tetramethyl xylylene diisocyanate, tetramethylene diisocyanate, hexamethylene diisocyanate, lysine diisocyanate ester, 1,4-cyclohexylene diisocyanate, 4,4'-dicyclohexylmethane diisocyanate, 3,3-dimethoxy-4,4'-biphenylene diisocyanate, 1,5-naphthalene diisocyanate, and isophorone diisocyanate. These may be used alone or in combination of two or more kinds thereof.

Further, the polyisocyanate used in the member according to the first embodiment of the present invention may be any of a biuret (dimer) type, an isocyanurate (trimer) type, an adduct type, a bifunctional type, or a modified product of these in addition to a single polyisocyanate.

Further, a terminal isocyanato group-containing compound obtained by reacting an excessive amount of these isocyanate compounds with a low-molecular-weight active hydrogen compound such as ethylene glycol, propylene glycol, trimethylolpropane, glycerin, sorbitol, ethylenediamine, monoethanolamine, diethanolamine, or triethanolamine or a high-molecular-weight active hydrogen compound such as various polyester polyols, polyether polyols, or polyamides is exemplified.

Examples of commercially available products of the polyisocyanate are shown below with the trade names thereof.

DURANATE Series (manufactured by Asahi Kasei Corporation) (DURANATE D101, DURANATE D201, DURANATE A101, DURANATE A201H, DURANATE 24A-100, DURANATE 22A-75P, DURANATE 21S-75E, DURANATEPA-100, DURANATE TKA-100, DURANATE MFA-75B, DURANATE MHG-80B, DURANATE TUL-100, DURANATE TLA-100, DURANATE TSA-100, DURANATE TSS-100, DURANATE TSE-100, DURANATE P301-75E, DURANATE E402-80B, DURANATE E405-70B, and DURANATE E700-100)

CORONATE Series and MILLIONATE Series (manufactured by Nippon Polyurethane Industry Co., Ltd.) (CORONATE L, CORONATE L-45E, CORONATE L-55E, CORONATE 2030, CORONATE 2031, CORONATE 2096, CORONATE 2233, CORONATE 2234, CORONATE 2298, CORONATE 2503, CORONATE 2507, CORONATE 2513, CORONATE 2515, CORONATE 3041, CORONATE AP-M, CORONATE HL, CORONATE HL-S, CORONATE HK, CORONATE HX, CORONATE HX-T, CORONATE HXLV, CORONATE HXR, MILLIONATE MT, MILLIONATE MTL, MILLIONATE MR, MILLIONATE MR100, MILLIONATE MR200, MILLIONATE MR300, MILLIONATE MR400, and MILLIONATE MS-50)

In addition, the polyisocyanates described in "Crosslinking Agent Handbook" (written by Minzo Yamashita, Touske Kaneko, first edition, 1981, Taiseisha Ltd.) are suitably used. These polyisocyanates may be used alone or in combination of two or more kinds thereof.

Among the polyisocyanates described above, from the viewpoints of the reactivity of the isocyanato group and the hardness of the coated film to be formed, at least one of 1,6-hexamethylene diisocyanate, isophorone diisocyanate, 2,4-tolylene diisocyanate, 2,6-tolylene diisocyanate, m-xylylene diisocyanate, or 4,4'-diphenylmethane diisocyanate is preferable.

The mass ratio between the hydrophilic polymer and the polyisocyanate (mass of hydrophilic polymer:mass of polyisocyanate) in the composition containing the hydrophilic polymer and the polyisocyanate is not particularly limited, but is preferably 1:0.01 to 1, more preferably 1:0.025 to 0.5, and particularly preferably 1:0.05 to 0.25. In a case where the mass ratio thereof is in the above-described range, the flexibility of the film formed of the composition containing the hydrophilic polymer and the polyisocyanate is improved.

In the member according to the embodiment of the present invention, the composition film is considered to be a gel film exhibiting the slipperiness at the time of wetting. In this gel film, the hydrophilic polymer and the polyisocyanate may be present in the form of a mixture. In other words, the functional group of the hydrophilic polymer may react with the isocyanato group of the polyisocyanate to form a bond (for example, a urethane bond) or may not react with the isocyanato group.

Further, in the member according to the first embodiment of the present invention, the functional group of the hydrophilic polymer in the composition film may react with the reactive functional group of the silicone base material to form a bond (for example, a urethane bond) or may not react with the reactive functional group. Further, the polyisocyanate in the composition film may react with the reactive functional group of the silicone base material to form a bond (for example, a urethane bond) or may not react with the reactive functional group.

The thickness of the composition film is not particularly limited, but is preferably in a range of 0.01 to 100 μm and more preferably in a range of 0.1 to 50 μm.

Next, the medical lubricating member according to the second embodiment of the present invention will be described.

The silicone base material used for the member according to the second embodiment of the present invention has the same definition as that for the silicone base material used for the member according to the first embodiment of the present invention except that the silicone base material does not contain the reactive functional group, and the preferable ranges are the same as described above. Further, the lubricating coated film used for the member according to the second embodiment of the present invention has the same definition as that for the lubricating coated film used for the member according to the first embodiment of the present invention, and the preferable ranges are the same as described above.

As described above, the silicone base material used for the member according to the second embodiment of the present invention includes an adhesive layer on at least one surface thereof. Hereinafter, this adhesive layer will be described.

(Adhesive Layer)

The adhesive layer used for the member according to the second embodiment of the present invention is not particularly limited as long as the adhesive layer contains a reactive functional group in the surface on which the lubricating coated film is laminated and can be formed by coating the surface of the silicone base material with a silane coupling agent, a polymer having a polysiloxane structure, or modified silicone. Further, the silane coupling agent, the polymer having a polysiloxane structure, and the modified silicone (hereinafter, also referred to as an adhesive component) may be respectively used alone or in combination of two or more kinds thereof.

Further, in the member according to the second embodiment of the present invention, since the reactive functional group forms a covalent bond or a hydrogen bond together with the hydrophilic polymer or polyisocyanate to be laminated, at least one of an amino group, an isocyanato group, a glycidyl group, a hydroxyl group, a carboxy group, a formyl group, an acid anhydride group, or an oxazoline ring (oxazolyl group) is preferable, and a hydroxyl group, an amino group, or a carboxy group is more preferable as the reactive functional group.

Further, the thickness of the adhesive layer is not particularly limited, but is preferably in a range of 0.001 to 50 μm and more preferably in a range of 0.01 to 10 μm.

—Silane Coupling Agent—

Examples of the silane coupling agent include the followings.

2-(3,4-epoxycyclohexyl)ethyltrimethoxysilane 3-glycidoxypropylmethyldimethoxysilane 3-glycidoxypropyltrimethoxysilane 3-glycidoxypropylmethyl diethoxysilane 3-glycidoxypropyltriethoxysilane N-2-(aminoethyl)-3-aminopropylmethyldimethoxysilane N-2-(aminoethyl)-3-aminopropyltrimethoxysilane 3-aminopropyltrimethoxysilane 3-aminopropyltriethoxysilane 3-triethoxysilyl-N-(1,3-dimethyl-butylidene)propylamine N-phenyl-3-aminopropyltrimethoxysilane Tris-(trimethoxysilylpropyl)isocyanurate 3-isocyanatepropyltriethoxysilane 3-trimethoxysilylpropylsuccinic anhydride N,N-bis(2-hydroxyethyl)-3-aminopropyltriethoxysilane —Polymer Having Polysiloxane Structure—

The polymer having a polysiloxane structure contains an acrylic acid component, an acrylic acid ester component, an acrylamide component, and/or a styrene component (at least one component of an acrylic acid component, an acrylic acid ester component, an acrylamide component, or a styrene component) in addition to the component having a polysiloxane structure, as a constituent component thereof.

The polymer having a polysiloxane structure contains a reactive functional group in a molecule.

It is preferable that the reactive functional group is contained in the acrylic acid component, the acrylic acid ester component, the acrylamide component, and/or the styrene component which is a constituent component of the polymer having a polysiloxane structure.

As the polymer having a polysiloxane structure, a graft polymer having the polysiloxane structure in a graft chain is preferable. It is preferable that this graft polymer is a structure having a structural unit represented by Formula (1) which has a polysiloxane structure in a graft chain, a structural unit represented by Formula (2) as an acrylic acid component or an acrylic acid ester component, a structural unit represented by Formula (3) as an acrylamide component, and/or a structural unit represented by Formula (4) as a styrene component (at least one structural unit of a structural unit represented by Formula (2) as an acrylic acid component or an acrylic acid ester component, a structural unit represented by Formula (3) as an acrylamide component, or a structural unit represented by Formula (4) as a styrene component).

—Structural Unit Having Polysiloxane Structure in Graft Chain—

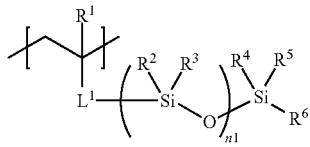

Formula (1)

In Formula (1), $R^1$ to $R^6$ represent a hydrogen atom or an organic group. Examples of the organic group which can be employed as $R^1$ to $R^6$ include an alkyl group, a cycloalkyl group, an alkenyl group, an aryl group, a heteroaryl group, an alkoxy group, an aryloxy group, a heteroaryloxy group, an alkylthio group, an arylthio group, a heteroarylthio group, an alkylamino group, an arylamino group, a heteroarylamino group, an alkyloxycarbonyl group, an aryloxycarbonyl group, a heteroaryloxycarbonyl group, an alkylaminocarbonyl group, an arylaminocarbonyl group, a heteroarylaminocarbonyl group, and a halogen atom. Among these, an alkyl group, a cycloalkyl group, an alkenyl group, or an aryl group is preferable.

The number of carbon atoms of the alkyl group which can be employed as $R^1$ to $R^6$ is preferably in a range of 1 to 10, more preferably in a range of 1 to 4, still more preferably 1 or 2, and particularly preferably 1. Specific examples of this alkyl group include methyl, ethyl, n-propyl, isopropyl, n-butyl, isobutyl, n-hexyl, n-octyl, 2-ethylhexyl, and n-decyl.

The number of carbon atoms of the ring structure in the cycloalkyl group which can be employed as $R^1$ to $R^6$ is preferably in a range of 3 to 10, more preferably in a range of 5 to 10, and still more preferably 5 or 6. Further, as this cycloalkyl group, a 3-membered ring, a 5-membered ring, or a 6-membered ring is preferable, and a 5-membered ring or a 6-membered ring is more preferable. Specific examples of the cycloalkyl group which can be employed as $R^1$ to $R^6$ include cyclopropyl, cyclopentyl, and cyclohexyl.

The number of carbon atoms of the alkenyl group which can be employed as $R^1$ to $R^6$ is preferably in a range of 2 to 10, more preferably in a range of 2 to 4, and still more preferably 2. Specific examples of the alkenyl group include vinyl, allyl, and butenyl.

The number of carbon atoms of the ring structure in the aryl group which can be employed as $R^1$ to $R^6$ is preferably in a range of 6 to 12, more preferably in a range of 6 to 10, and still more preferably 6 to 8. Specific examples of this aryl group include phenyl, tolyl, and naphthyl.

As the heteroaryl group which can be employed as $R^1$ to $R^6$, a heteroaryl group having a 5-membered ring or a 6-membered ring which has at least one oxygen atom, sulfur atom, or nitrogen atom is more preferable. Specific examples of this heteroaryl group include 2-pyridyl, 2-thienyl, 2-furanyl, 3-pyridyl, 4-pyridyl, 2-imidazolyl, 2-benzoimidazolyl, 2-thiazolyl, 2-benzothiazolyl, and 2-oxazolyl.

The preferable forms of the aryl group constituting the aryloxy group, the arylthio group, the arylamino group, the aryloxycarbonyl group, and the arylaminocarbonyl group which can be employed as $R^1$ to $R^6$ are the same as the preferable forms of the aryl group which can be employed as $R^1$ to $R^6$.

The preferable forms of the heteroaryl group constituting the heteroaryloxy group, the heteroarylthio group, the heteroarylamino group, the heteroaryloxycarbonyl group, and the heteroarylaminocarbonyl group which can be employed as $R^1$ to $R^6$ are the same as the preferable forms of the heteroaryl group which can be employed as $R^1$ to $R^6$.

The preferable forms of the alkyl group constituting the alkoxy group, the alkylthio group, the alkylamino group, the alkyloxycarbonyl group, and the alkylaminocarbonyl group which can be employed as $R^1$ to $R^6$ are the same as the preferable forms of the alkyl group which can be employed as $R^1$ to $R^6$.

Examples of the halogen atom which can be employed as $R^1$ to $R^6$ include a fluorine atom, a chlorine atom, a bromine atom, and an iodine atom. Among these, a fluorine atom or a bromine atom is preferable.

In a case where $R^1$ to $R^6$ represents an organic group, a form in which the organic group has a substituent may be employed.

$R^1$ to $R^6$ represent preferably an alkyl group, an alkenyl group, or an aryl group and more preferably an alkyl group having 1 to 4 carbon atoms. Among these, it is preferable that $R^1$ to $R^5$ represent a methyl group, and $R^6$ represents a butyl group.

In Formula (1), $L^1$ represents a single bond or a divalent linking group.

The divalent linking group which can be employed as L1 is not particularly limited as long as the effects of the present invention are exhibited. In a case where $L^1$ represents a divalent linking group, the molecular weight of $L^1$ is preferably in a range of 10 to 200, more preferably in a range of 20 to 100, and still more preferably in a range of 30 to 70.

In a case where $L^1$ represents a divalent linking group, for example, a divalent linking group formed by combining two or more divalent groups selected from an alkylene group, an arylene group, —C(=O)—, —O—, and —$NR^L$— is preferable. $R^L$ represents a hydrogen atom or a substituent. In a case where $R^L$ represents a substituent, an alkyl group is preferable as this substituent. As this alkyl group, an alkyl group having 1 to 6 carbon atoms is preferable, an alkyl group having 1 to 4 carbon atoms is more preferable, and methyl or ethyl is still more preferable.

The alkylene group which can form $L^1$ may be linear or branched. The number of carbon atoms of this alkylene group is preferably in a range of 1 to 10, more preferably in a range of 1 to 6, and still more preferably in a range of 1 to 3.

Further, as the ring structure of the alkylene group which can form $L^1$, a ring structure having 6 to 20 carbon atoms is preferable, a ring structure having 6 to 15 carbon atoms is more preferable, a ring structure having 6 to 12 carbon atoms is still more preferable, and a phenylene group is even still more preferable.

It is preferable that L represents a divalent linking group formed by combining two or more divalent groups selected from an alkylene group, —C(=O)—, —O—, and —$NR^L$—.

In Formula (1), n1 is an integer of 3 to 10000. n1 is preferably an integer of 135 to 10000, more preferably an integer of 150 to 5000, and still more preferably an integer of 200 to 1000.

In the polymer having a polysiloxane structure, the content of the structural unit represented by Formula (1) is preferably in a range of 1% to 70% by mass, more preferably in a range of 5% to 60% by mass, and still more preferably in a range of 10% to 50% by mass.

The structural unit represented by Formula (1) can be introduced to the polymer having a polysiloxane structure using a macromonomer having a specific structure as a raw material. This macromonomer can be synthesized according to a method of the related art, or a commercially available product can also be used. Examples of the commercially available product thereof include X-22-174ASX, X-22-

174BX, KF-2012, X-22-2426, and X-22-2404 (all trade names, manufactured by Shin-Etsu Chemical co., Ltd.); AK-5, AK-30, and AK-32 (all trade names, manufactured by Toagosei Co., Ltd.); and MCR-M07, MCR-M11, MCR-M17, and MCR-M22 (all trade names, manufactured by Gelest, Inc.).

—Acrylic Acid Component or Acrylic Acid Ester Component—

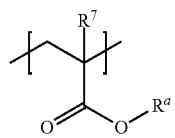

Formula (2)

In Formula (2), $R^7$ and $R^a$ represent a hydrogen atom or an organic group.

Examples of the forms of the organic group which can be employed as $R^7$ include the forms of the organic group which can be employed as $R^1$ in Formula (1). Among these, $R^7$ preferably represents a hydrogen atom or an alkyl group. The number of carbon atoms of the alkyl group is preferably in a range of 1 to 10, more preferably in a range of 1 to 4, still more preferably 1 or 2, and particularly preferably 1. Specific examples of this alkyl group include methyl, ethyl, n-propyl, isopropyl, n-butyl, isobutyl, n-hexyl, n-octyl, 2-ethylhexyl, and n-decyl.

Examples of the forms of the organic group which can be employed as $R^a$ include the forms of the organic group which can be employed as $R^1$ in Formula (1). Among the examples, it is preferable that $R^a$ represents a hydrogen atom, an alkyl group, or an aryl group. The number of carbon atoms of the alkyl group which can be employed as $R^a$ is preferably in a range of 1 to 10 and more preferably in a range of 1 to 6. Specific examples of the alkyl group include methyl, ethyl, n-propyl, isopropyl, n-butyl, isobutyl, n-hexyl, n-octyl, 2-ethylhexyl, and n-decyl.

The number of carbon atoms of the aryl group which can be employed as $R^a$ is preferably in a range of 6 to 12, more preferably in a range of 6 to 10, still more preferably in a range of 6 to 8, and particularly preferably 6. Specific examples of this aryl group include phenyl, tolyl, and naphthyl.

In a case where $R^7$ and $R^a$ represent an organic group, a form in which the organic group has a substituent may be employed. In a case where the polymer having a polysiloxane structure has structural units represented by Formula (2), it is preferable that at least some structural units from among the structural units represented by Formula (2) in the polymer having a polysiloxane structure contain a reactive functional group described above as a substituent.

Further, in the structural units represented by Formula (2) which are present in the polymer having a polysiloxane structure, in a case where $R^a$ represents an alkyl group having a substituent, a form in which $R^a$ is represented by Formula (5) in at least some structural units from among the structural units is also preferable.

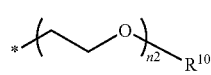

Formula (5)

In Formula (5), n2 is an integer of 1 to 10000. n2 is preferably an integer of 1 to 8000, more preferably an integer of 1 to 5000, and still more preferably an integer of 1 to 3000.

$R^{10}$ represents a hydrogen atom or an organic group. Examples of the forms of the organic group which can be employed as $R^{10}$ include the forms of the organic group which can be employed as $R^1$ in Formula (1). In a case where $R^{1'}$ represents an organic group, a form in which the organic group has a substituent may be employed. It is preferable that $R^{10}$ represents a hydrogen atom or an alkyl group. Specific examples of this alkyl group include methyl, ethyl, n-propyl, isopropyl, n-butyl, isobutyl, n-hexyl, n-octyl, 2-ethylhexyl, and n-decyl.

The symbol "*" represents a bonding site with respect to an oxygen atom (—O—) in Formula (2).

In at least some structural units from among the structural units represented by Formula (2) which are present in the polymer having a polysiloxane structure, it is also preferable that $R^a$ represents a nitrogen-containing organic group. The molecular weight of the nitrogen-containing organic group is preferably in a range of 10 to 200 and more preferably in a range of 20 to 100. As the nitrogen-containing organic group, an amino group (including a substituted amino group) is preferable. Preferred examples of the nitrogen-containing organic group include an alkylamino group, an alkylaminoalkyl group, an arylamino group, an arylaminoalkyl group, a heteroarylamino group, and a heteroarylaminoalkyl group.

—Acrylamide Component—

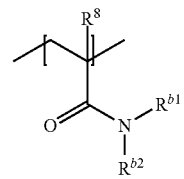

Formula (3)

In Formula (3), $R^8$, $R^{b1}$, and $R^{b2}$ represent a hydrogen atom or an organic group.

Examples of the forms of the organic group which can be employed as $R^8$ include the forms of the organic group which can be employed as $R^1$ in Formula (1). $R^8$ represents preferably a hydrogen atom or an alkyl group and more preferably an alkyl group. The number of carbon atoms of the alkyl group is preferably in a range of 1 to 10, more preferably in a range of 1 to 4, still more preferably 1 or 2, and particularly preferably 1. Specific examples of this alkyl group include methyl, ethyl, n-propyl, isopropyl, n-butyl, isobutyl, n-hexyl, n-octyl, 2-ethylhexyl, and n-decyl.

Examples of the organic groups which can be employed as $R^{b1}$ and $R^{b2}$ include the organic groups which can be employed as $R^1$ in Formula (1). Among the examples, it is preferable that $R^{b1}$ and $R^{b2}$ represent a hydrogen atom, an alkyl group, or an aryl group. The number of carbon atoms of the aryl group is preferably in a range of 6 to 12, more preferably in a range of 6 to 10, still more preferably in a range of 6 to 8, and particularly preferably 6. Specific examples of this aryl group include phenyl, tolyl, and naphthyl.

In a case where $R^8$, $R^{b1}$, and $R^{b2}$ represent an organic group, a form in which the organic group has a substituent may be employed. In a case where the polymer having a polysiloxane structure has structural units represented by Formula (3), it is preferable that at least some structural units from among the structural units represented by Formula (3) in the polymer having a polysiloxane structure contain a reactive functional group described above as a substituent.

—Styrene Component—

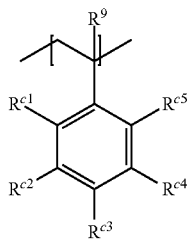

Formula (4)

In Formula (4), $R^9$ represents a hydrogen atom or an organic group. $R^{c1}$ to $R^{c5}$ represent a hydrogen atom, a halogen atom, or an organic group.

Examples of the forms of the organic group which can be employed as $R^9$ include the forms of the organic group which can be employed as $R^1$ in Formula (1). Among these, it is preferable that $R^9$ represents a hydrogen atom.

Examples of the forms of the organic group which can be employed as $R^{c1}$ to $R^{c5}$ include the forms of the organic group which can be employed as $R^1$ in Formula (1). The halogen atom which can be employed as $R^{c1}$ to $R^{c5}$ is not particularly limited. Among examples of the halogen atom, a fluorine atom or a bromine atom is preferable, and a fluorine atom is more preferable. It is preferable that $R^{c1}$ to $R^{c5}$ represent a hydrogen atom, an alkyl group, or a halogen atom. The number of carbon atoms of the alkyl group is preferably in a range of 1 to 10, more preferably in a range of 1 to 4, still more preferably 1 or 2, and particularly preferably 1. Specific examples of this alkyl group include methyl, ethyl, n-propyl, isopropyl, n-butyl, isobutyl, n-hexyl, n-octyl, 2-ethylhexyl, and n-decyl.

In a case where $R^9$ and $R^{c1}$ to $R^{c5}$ represent an organic group, a form in which the organic group has a substituent may be employed. In a case where the polymer having a polysiloxane structure has structural units represented by Formula (4), it is preferable that at least some structural units from among the structural units represented by Formula (4) in the polymer having a polysiloxane structure contain a reactive functional group described above as a substituent.

In a case where the polymer having a polysiloxane structure has a structural unit represented by any of Formulae (2) to (4), the total amount of these structural units in the polymer having a polysiloxane structure is preferably in a range of 10% to 90% by mass, more preferably in a range of 15% to 80% by mass, and still more preferably in a range of 20% to 70% by mass.

Further, in a case where the polymer having a polysiloxane structure is represented by any of Formulae (2) to (4) and has a structural unit that contains the reactive functional group, the content of such a structural unit in the polymer having a polysiloxane structure is preferably in a range of 5% to 70% by mass, more preferably in a range of 10% to 50% by mass, and still more preferably in a range of 15% to 30% by mass.

The polymer having a polysiloxane structure can be synthesized according to a method of the related art. For example, the polymer is obtained by reacting a monomer leading a desired structural unit with a polymerization initiator according to a method of the related art. As the polymerization reaction, any of anionic polymerization, cationic polymerization, and radical polymerization may be used, but radical polymerization is preferable.

It is also preferable that the polymer having a polysiloxane structure has a crosslinked structure through a crosslinking agent. In this case, it is preferable that the crosslinking agent is a crosslinking agent (polymeric crosslinking agent) having a structural unit represented by Formula (6) and/or a crosslinking agent represented by formula (7). The adhesive layer is cured so that the mechanical strength can be improved by forming the crosslinked structure using these crosslinking agents. These crosslinking agents typically interact with the reactive functional group included in each of the above-described structural units or react with the reactive functional group to form a crosslinked structure in the polymer having a polysiloxane structure. The crosslinking reaction can be carried out according to a method of the related art depending on the kind of the group contributing to the crosslinking reaction.

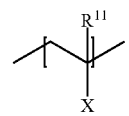

Formula (6)

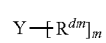

Formula (7)

In Formula (6), $R^{11}$ represents a hydrogen atom or an organic group. In a case where $R^{11}$ represents an organic group, a form in which the organic group has a substituent may be employed. It is preferable that $R^{11}$ represents a hydrogen atom or an alkyl group (an alkyl group having preferably 1 to 5 carbon atoms and more preferably 1 to 3 carbon atoms). X represents a hydroxy group, a carboxy group, an amino group, an isocyanato group, an oxazoline ring, an epoxy group, a vinyl group, an ethynyl group, a sulfanyl group, an azide group, a trialkoxysilyl group, or a group having an acid anhydride structure. X may represent a group having a substituent.

Examples of the crosslinking agent represented by Formula (6) include an oxazoline ring-containing polymer (trade name: EPOCROS (registered trademark), manufactured by Nippon Shokubai Co., Ltd.). The oxazoline ring-containing polymer is a polymer formed of the following structural unit. In the present specification, Me represents methyl.

Further, in a case where the crosslinking agent is a polymer and contains an acrylic acid component, an acrylic acid ester component, an acrylamide component, or a styrene component as a constituent component, these components are respectively included in the acrylic acid component, the acrylic acid ester component, the acrylamide component, or the styrene component defined in the present invention.

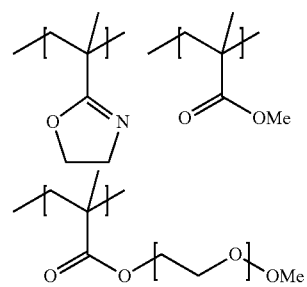

In Formula (7), Y represents an m-valent linking group. It is preferable that Y represents a hydrocarbon group having preferably 2 to 20 carbon atoms and more preferably 2 to 15 carbon atoms. This hydrocarbon group may have heteroatoms in the hydrocarbon chain thereof. Examples of the heteroatoms include O, S, N, and Ti. m is an integer of 2 or greater, preferably an integer or 2 to 8, and more preferably an integer of 2 to 4. $R^{dm}$ has the same definition as that for X in Formula (6).

Examples of the crosslinking agent represented by Formula (7) include a polyisocyanate compound (preferably a diisocyanate compound), a silane coupling agent, and a titanium coupling agent. An example of the crosslinking agent represented by Formula (7) is shown below.

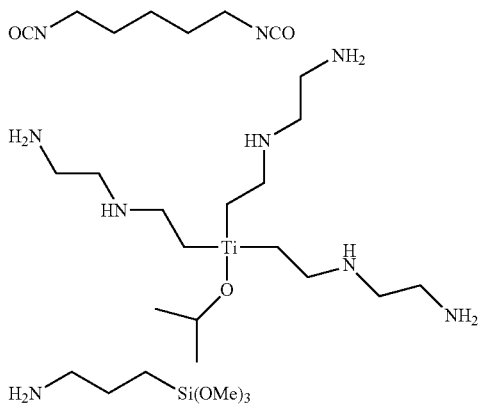

In a case where the polymer having a polysiloxane structure has a crosslinked structure through a crosslinking agent, the proportion of the crosslinking agent components (the components derived from the crosslinking agent) in the polymer having a polysiloxane structure with the crosslinked structure is preferably in a range of 30% to 90% by mass and more preferably in a range of 40% to 70% by mass.

The mass average molecular weight of the polymer having a polysiloxane structure (the mass average molecular weight of the polymer having a polysiloxane structure in a state before being crosslinked in a case where the polymer having a polysiloxane structure has a crosslinked structure through a crosslinking agent) is preferably in a range of 10000 to 300000, more preferably in a range of 30000 to 150000, and still more preferably in a range of 40000 to 120000.

Specific examples of the polymer having a polysiloxane structure include SYMAC (registered trademark, manufactured by Toagosei Co., Ltd.) Series (for example, SYMAC US-450), ACRIT (registered trademark, manufactured by Taisei Fine Chemical Co., Ltd.) Series (for example, ACRIT 8-BS-9000), CHALINE (registered trademark, manufactured by Nissin Chemical Co., Ltd.) Series, and acrylic silicone (manufactured by Shin-Etsu Polymer Co., Ltd.).

—Modified Silicone—

Examples of the modified silicone include terminal-modified silicone oil obtained by being modified by a glycidyl group, an amino group, a carboxy group, an acid anhydride group, or an isocyanato group; and a silicone-based surfactant. In addition, the compounds described in "Silicone Handbook" (written by Kunio Ito, first edition, 1990, Nikkan Kogyo Shimbun, Ltd.) can also be used.

The content of the adhesive component in the adhesive layer is preferably 5% by mass or greater, more preferably 10% by mass or greater, and still more preferably 20% by mass or greater. Further, the content of the adhesive component in the adhesive layer is also preferably 40% by mass or greater, preferably 60% by mass or greater, or preferably 80% by mass or greater. The upper limit thereof may be 100% by mass. In a case where the adhesive layer contains a component other than the polymer having a polysiloxane structure, examples of the component other than the polymer having a polysiloxane structure include a polymer binder, a surfactant, polymer fine particles, and inorganic fine particles.

It is preferable that the adhesive layer in the member according to the second embodiment of the present invention has excellent wettability particularly with respect to the silicone base material and is formed using alkoxy-modified silicone that is capable of forming a hydroxyl group on a surface thereof. Specific examples thereof include RITA-SURF (trade name, manufactured by Rita Fine Co., Ltd.); X-93-1710 and X-93-1755-1 (both trade names, manufactured by Shin-Etsu Chemical Co., Ltd.); and FZ-3704 and AY42-163 (both trade names, manufactured by Dow Corning Toray Co., Ltd.).

It is preferable that the silicone base material used in the present invention is a tubular silicone base material.

It is preferable that the member according to the first embodiment of the present invention is formed such that the lubricating coated film is laminated at least on the inside of the tubular silicone base material, that is, on the inner peripheral surface thereof. Further, it is preferable that the member according to the second embodiment of the present invention is formed such that the adhesive layer is provided at least on the inner peripheral surface of the tubular silicone base material, and the lubricating coated film is laminated on a side of the adhesive layer opposite to the surface where the tubular silicone base material is in contact. Hereinafter, these forms will be referred to as a form in which the member according to the embodiment of the present invention includes the lubricating coated film inside the tubular silicone base material.

Meanwhile, both of the form in which the member according to the first embodiment of the present invention is formed such that the lubricating coated film is laminated on the outside of the tubular silicone base material, that is, on the outer peripheral surface thereof and the form in which the member according to the second embodiment of the present invention is formed such that the adhesive layer is provided on the outer peripheral surface of the tubular silicone base material, and the lubricating coated film is laminated on a side of the adhesive layer opposite to the surface where the tubular silicone base material is in contact will be referred to as a form in which the member according to the embodiment of the present invention includes the lubricating coated film on the outside of the tubular silicone base material.

Further, both of the form in which the member according to the first embodiment of the present invention is formed such that the lubricating coated film is laminated on the inner peripheral surface and the outer peripheral surface of the tubular silicone base material and the form in which the member according to the second embodiment of the present invention includes the adhesive layer on the inner peripheral surface and the outer peripheral surface of the tubular silicone base material, and the lubricating coated film is laminated on a side of the adhesive layer opposite to the surface where the tubular silicone base material is in contact will be referred to as a form in which the member according to the embodiment of the present invention includes the lubricating coated film on both sides of the tubular silicone base material.

In the member according to the second embodiment of the present invention, the functional group contained in the hydrophilic polymer of the composition film may react with the reactive functional group in the adhesive layer to form a bond (such as a urethane bond) or may not react with the reactive functional group. Further, the polyisocyanate in the composition film may react with the reactive functional group in the adhesive layer to form a bond (such as a urethane bond) or may not react with the reactive functional group.

<Applications>

It is preferable that the member according to the embodiment of the present invention is used as a member for a balloon, a connector, a rubber component for a medical device, a medical tube (such as an angiography tube, a tracheal tube, a feeding tube, or a tube for a urinary system), an endoscope overtube, or a catheter.

The applications in which the silicone base material is tubular are described below.

It is preferable that the form in which the member according to the embodiment of the present invention includes the lubricating coated film on the inside of the tubular silicone base material is used for a medical tube, an endoscope overtube, and a catheter.

Further, it is preferable that the form in which the member according to the embodiment of the present invention includes the lubricating coated film on the outside of the tubular silicone base material is used for a medical tube and a catheter.

Further, it is preferable that the form in which the member according to the embodiment of the present invention includes the lubricating coated film on both sides of the tubular silicone base material is used for a medical tube and a catheter.

<Method of Producing Medical Lubricating Member>

A method of producing the member according to the embodiment of the present invention is not particularly limited. Hereinafter, an example of a method of producing the member according to the first embodiment of the present invention and an example of a method of producing the member according to the second embodiment of the present invention will be described.

—Example of Method of Producing Member According to First Embodiment—

[Preparation of Liquid]

A composition obtained by dissolving the hydrophilic polymer and the polyisocyanate in an organic solvent is prepared.

[Introduction of Reactive Functional Group]

A tubular silicone rubber base material in which a hydroxy group and a carboxy group have been introduced to the inner peripheral surface and the outer peripheral surface of the tubular silicone rubber is prepared by irradiating the inner peripheral surface and the outer peripheral surface of the tubular silicone rubber with active energy rays.

[Lamination of Lubricating Coated Film]

The tubular silicone rubber base material is immersed in the composition at room temperature for 1 second to 60 minutes and heated and dried in a temperature range of 25° C. to 180° C. for 1 to 120 minutes.

Further, a step of applying the composition to the tubular silicone rubber base material may be performed according to a method of the related art. For example, the composition can be applied to the inner peripheral surface of the tubular silicone rubber by being poured into the tube of the tubular silicone rubber.

—Example of Method of Producing Member According to Second Embodiment—

[Preparation of Liquid]

A composition (a) obtained by dissolving the polymer having a polysiloxane structure in an organic solvent is prepared. In addition, a composition (b) obtained by dissolving the hydrophilic polymer and the polyisocyanate in an organic solvent is prepared.

[Formation of Adhesive Layer]

The tubular silicone rubber is immersed in the composition (a) at room temperature for 1 second to 60 minutes and heated and dried in a temperature range of 25° C. to 180° C. for 1 to 120 minutes. A tubular silicone rubber base material in which a hydroxyl group (silanol group) has been introduced to the inner peripheral surface and the outer peripheral surface of the tubular silicone rubber is prepared by performing a treatment on the tubular silicone rubber using 10% to 40% of hydrochloric acid for 30 minutes to 24 hours.

[Lamination of Lubricating Coated Film]

The lamination is carried out using the composition (b) in the same manner as in the first embodiment.

Examples of the organic solvent include an ether solvent such as dibutyl ether, dimethoxymethane, dimethoxyethane, diethoxyethane, propylene oxide, 1,4-dioxane, 1,3-dioxolane, 1,3,5-trioxane, tetrahydrofuran, anisole, or phenentole; a ketone solvent such as acetone, methyl ethyl ketone, diethyl ketone, dipropyl ketone, diisobutyl ketone, methyl isobutyl ketone, cyclopentanone, cyclohexanone, methyl cyclohexanone, or dimethyl cyclohexanone; an ester solvent such as ethyl formate, propyl formate, n-pentyl formate, methyl acetate, ethyl acetate, methyl propionate, ethyl propionate, n-pentyl acetate, or γ-butyrolactone; an alcohol solvent such as methanol, ethanol, I-propanol, 2-propanol, 1-butanol, 2-butanol, tert-butanol, 1-pentanol, 2-methyl-2-butanol, or cyclohexanol; aromatic hydrocarbon such as xylene or toluene; a halogenated hydrocarbon solvent such as methylene chloride, chloroform, or 1,1-dichloroethane; an amide-based solvent such as N-methyl-2-pyrrolidone (NMP), N,N-dimethylformamide (DMF), or N,N-dimethylacetamide (DMAc); a nitrile solvent such as acetonitrile; and an organic solvent containing two or more kinds of functional groups such as methyl 2-methoxy acetate, methyl 2-ethoxy acetate, ethyl 2-ethoxy acetate, ethyl 2-ethoxy propionate, 2-methoxy ethanol, 2-propoxy ethanol, 2-butoxy ethanol, 1,2-diacetoxy acetone, acetyl acetone, diacetone alcohol, methyl acetoacetate, N-methylpyrrolidone, propylene glycol monomethyl ether acetate, or ethyl acetoacetate.

EXAMPLES

Hereinafter, the present invention will be described in more detail based on the examples. Further, the present invention is not limitatively interpreted by the examples. In addition, the "room temperature" indicates 25° C.

Example 1

A composition (b1) was prepared by dissolving 2.0 g of polyvinylpyrrolidone (trade name: K-90, manufactured by Wako Pure Chemical Industries, Ltd.) and 1.0 g of HDI (1,6-hexamethylene diisocyanate, manufactured by Wako Pure Chemical Industries, Ltd.) in 100 g of chloroform (manufactured by Tokyo Chemical Industry Co., Ltd.).

A silicone rubber sheet (trade name: KE-880-U, hardness of 80 A, manufactured by Shin-Etsu Chemical Co., Ltd.) having a length of 70 mm, a width of 40 mm, and a thickness of 500 µm was immersed in RITASURF (trade name, manufactured by Rita Fine Co., Ltd.). RITASURF which had been applied to the silicone rubber sheet was heated and dried at 150° C. for 5 minutes to prepare a silicone base material on which an adhesive layer containing a reactive functional group (hydroxyl group) was laminated. This silicone base material was immersed in the composition (b1) at room temperature (25° C.) for 3 minutes and heated and dried at 60° C. for 30 minutes and 135° C. for 30 minutes to form a lubricating coated film, thereby preparing a sheet of Example 1.

The thickness of each adhesive layer of the sheet of Example 1 was 0.2 µm and the thickness of each lubricating coated film of Example 1 was 11 µm.

Example 2

A composition (a2) was prepared by diluting 13.3 g of ACRIT 8BS-9000 (trade name, manufactured by Taisei Fine Chemical Co., Ltd.) with 86.7 g of 2-propanol. Further, a composition (b2) was prepared by dissolving 2.0 g of polyvinylpyrrolidone (trade name: K-90 manufactured by Wako Pure Chemical Industries, Ltd.) and 0.5 g of MDI (4,4'-diphenylmethane diisocyanate, manufactured by Tokyo Chemical Industry Co., Ltd.) in 100 g of chloroform (manufactured by Wako Pure Chemical Industries, Ltd.).

A silicone rubber sheet (trade name: KE-880-U, hardness of 80 A, manufactured by Shin-Etsu Chemical Co., Ltd.) having the same size as in Example 1 was immersed in the composition (a2) at room temperature for 3 minutes and dried at 150° C. for 30 minutes. Both surfaces of the silicone rubber sheet having an adhesive layer formed of the composition (a2) on each of both surfaces were treated with 20% hydrochloric acid for 3 hours. In this manner, a silicone base material on which an adhesive layer containing a reactive functional group (hydroxyl group) was laminated was prepared. This silicone base material was immersed in the composition (b2) at room temperature for 3 minutes and heated and dried at 60° C. for 30 minutes and 135° C. for 30 minutes to form a lubricating coated film, thereby preparing a sheet of Example 2.

The thickness of each adhesive layer of the sheet of Example 2 was 0.4 µm and the thickness of each lubricating coated film of Example 2 was 10 µm.

Example 3

A composition (a3) was prepared by diluting 25 g of SYMAC US-450 (trade name, manufactured by Toagosei Co., Ltd.) with 75 g of 2-propanol. Further, a composition (b3) was prepared by dissolving 2.0 g of hyaluronic acid (manufactured by Tokyo Chemical Industry Co., Ltd.) and 0.5 g of TDI (2,6-tolylene diisocyanate, manufactured by Wako Pure Chemical Industries, Ltd.) in 97.5 g of chloroform (manufactured by Wako Pure Chemical Industries, Ltd.).

A silicone rubber sheet (trade name: KE-880-U, hardness of 80 A, manufactured by Shin-Etsu Chemical Co., Ltd.) having the same size as in Example 1 was immersed in the composition (a3) at room temperature for 3 minutes and dried at 150° C. for 30 minutes. Both surfaces of the silicone rubber sheet having an adhesive layer formed of the composition (a3) on each of both surfaces were treated with 20% hydrochloric acid for 3 hours. In this manner, a silicone base material on which an adhesive layer containing a reactive functional group (a carboxy group or a hydroxyl group) was laminated was prepared. This silicone base material was immersed in the composition (b3) for 3 minutes and heated and dried at 60° C. for 30 minutes and 135° C. for 30 minutes to form a lubricating coated film, thereby preparing a sheet of Example 3.

The thickness of each adhesive layer of the sheet of Example 3 was 0.3 µm and the thickness of each lubricating coated film of Example 3 was 9 µm.

Example 4

A composition (b4) was prepared by dissolving 2.0 g of polyvinylpyrrolidone (trade name: K-90, manufactured by Wako Pure Chemical Industries, Ltd.) and 0.5 g of MDI (4,4'-diphenylmethane diisocyanate, manufactured by Tokyo Chemical Industry Co., Ltd.) in 97.5 g of chloroform (manufactured by Wako Pure Chemical Industries, Ltd.).

Both surfaces of a silicone rubber sheet (trade name: KE-880-U, hardness of 80 A, manufactured by Shin-Etsu Chemical Co., Ltd.) having the same size as in Example 1 were subjected to a plasma treatment in a vacuum state using a plasma irradiation device PDC-001 (trade name, manufactured by HARRICK Plasma) under the following conditions to obtain a silicone base material containing a carboxy group and a hydroxyl group. This silicone base material was immersed in the composition (b4) at room temperature for 3 minutes and heated and dried at 60° C. for 30 minutes and 135° C. for 30 minutes to form a lubricating coated film, thereby preparing a sheet of Example 4.

The thickness of each lubricating coated film of the sheet in Example 4 was 13 vtm.

(Conditions of Plasma Treatment)
Irradiation time: 3 minutes
Irradiation temperature: room temperature
Output: 13.56 MHz Example 5

A composition (a5) was prepared by diluting 13.3 g of ACRIT 8BS-9000 (trade name, manufactured by Taisei Fine Chemical Co., Ltd.) with 86.7 g of 2-propanol. Further, a composition (b5) was prepared by dissolving 2.0 g of a methyl vinyl ether-maleic acid anhydride copolymer (manufactured by Sigma-Aldrich Co. LLC.) and 0.5 g of MDI (4,4'-diphenylmethane diisocyanate, manufactured by Tokyo Chemical Industry Co., Ltd.) in 97.5 g of chloroform (manufactured by Wako Pure Chemical Industries, Ltd.).

A silicone rubber sheet (trade name: KE-880-U, hardness of 80 A, manufactured by Shin-Etsu Chemical Co., Ltd.) having the same size as in Example 1 was immersed in the composition (a5) at room temperature for 3 minutes and dried at 150° C. for 30 minutes. Both surfaces of the silicone rubber sheet having an adhesive layer formed of the composition (a5) on each of both surfaces were treated with 20% hydrochloric acid for 3 hours. In this manner, a silicone base material on which an adhesive layer containing a reactive functional group (hydroxyl group) was laminated was prepared. This silicone base material was immersed in the composition (b5) at room temperature for 3 minutes and heated and dried at 60° C. for 30 minutes and 135° C. for 30 minutes to form a lubricating coated film, thereby preparing a sheet of Example 5.

The thickness of each adhesive layer of the sheet of Example 5 was 0.2 µm and the thickness of each lubricating coated film of Example 5 was 13 µm.

Comparative Example 1

A sheet of Comparative Example 1 was prepared in the same manner as in Example 2 except that the adhesive layer was not provided.

Comparative Example 2

A solution (2c) was prepared by dissolving 1.0 g of MDI (4,4'-diphenylmethane diisocyanate, manufactured by Tokyo Chemical Industry Co., Ltd.) in 99 g of 2-butanone (manufactured by Wako Pure Chemical Industries, Ltd.). Further, a solution (2d) was prepared by dissolving 2.0 g of polyvinylpyrrolidone (trade name: K-90 manufactured by Wako Pure Chemical Industries, Ltd.) in 98 g of chloroform (manufactured by Wako Pure Chemical Industries, Ltd.).

Both surfaces of a urethane sheet (MIRACTRAN P490RSUI, trade name, manufactured by Tosoh Corporation) having a length of 70 mm, a width of 40 mm, and a thickness of 500 μm were subjected to a plasma treatment in the same manner as in Example 4 to obtain a urethane base material containing a carboxy group and a hydroxyl group. This urethane base material was immersed in the solution (2c) for 3 minutes and heated and dried at 60° C. for 30 minutes. Next, this urethane base material was immersed in the solution (2d) for 3 minutes and heated and dried at 60° C. for 120 minutes to form a lubricating coated film, thereby preparing a sheet of Comparative Example 2.

The thickness of each film on the silicone base material of the sheet in Comparative Example 2 was 12 μm.

Comparative Example 3

A sheet of Comparative Example 3 was prepared in the same manner as in Comparative Example 2 except that a silicone rubber sheet (trade name: KE-880-U, hardness of 80 A, manufactured by Shin-Etsu Chemical Co., Ltd.) having the same size as in Example 1 was used, and heating and drying of the silicone base material at 60° C. for 120 minutes were changed to heating and drying of the silicone base material at 60° C. for 30 minutes and 135° C. for 30 minutes.

The thickness of each film on the silicone base material of the sheet in Comparative Example 3 was 9 μm.

<Evaluation of Each Characteristic>

The following tests were performed on the sheets of Examples 1 to 5 and Comparative Examples 1 to 3.

[Slipperiness at Time of Wetting]

The test was performed using a continuous weight type scratch resistance strength tester (type: 18 type (manufactured by HEIDON)). In a state in which the prepared sheet was immersed in water, the dynamic friction coefficient (k) thereof was measured after a tetrafluoroethylene indenter was allowed to reciprocate once with a load of 1000 g, and the evaluation was performed based on the following evaluation standards. Further, the one-way distance was 30 mm, and the water temperature was 25° C.

(Evaluation Standard)
A: $\mu k < 0.03$
B: $0.03 < \mu k < 0.06$
C: $0.06 < \mu k < 0.1$
D: $0.1 < \mu k$ A and B described above are in an acceptable level.

[Durability at Time of Wetting]

The test was performed in the same manner as that for the slipperiness at the time of wetting except that the dynamic friction coefficient (k) was measured after a tetrafluoroethylene indenter was allowed to reciprocate 50 times.

(Evaluation Standard)
A: $\mu k < 0.03$
B: $0.03 < \mu k < 0.06$
C: $0.06 < \mu k < 0.1$
D: $0.1 < \mu k$ A and B described above are in an acceptable level.

The obtained results are collectively listed in Table 1.

TABLE 1

|  | Example 1 | Example 2 | Example 3 | Example 4 | Example 5 |
|---|---|---|---|---|---|
| Base material | Silicone rubber | Silicone rubber | Silicone rubber | Silicone rubber | Silicone rubber |
| Undercoat (adhesive layer) | RITASURF | ACRIT 8-BS-9000 | SYMAC US-450 | — | ACRIT 8-BS-9000 |
| Physical treatment | — | — | — | Plasma treatment | — |
| Reactive functional group | Hydroxyl group | Hydroxyl group | Carboxy group Hydroxyl group | Carboxy group Hydroxyl group | Hydroxyl group |
| Hydrophilic polymer | PVP | PVP | Hyaluronic acid | PVP | Methyl vinyl ether-maleic acid anhydride copolymer |
| Polyisocyanate | HDI | MDI | TDI | MDI | MDI |
| Step of forming lubricating coated film | Mixed coating of hydrophilic polymer and polyisocyanate | Mixed coating of hydrophilic polymer and polyisocyanate | Mixed coating of hydrophilic polymer and polyisocyanate | Mixed coating of hydrophilic polymer and polyisocyanate | Mixed coating of hydrophilic polymer and polyisocyanate |
| Slipperiness at time of wetting | A | A | B | A | B |
| Durability at time of wetting | B | A | A | B | A |

|  | Comparative Example 1 | Comparative Example 2 | Comparative Example 3 |
|---|---|---|---|
| Base material | Silicone rubber | Polyurethane | Silicone rubber |
| Undercoat (adhesive layer) | — | — | — |

TABLE 1-continued

| | | | |
|---|---|---|---|
| Physical treatment | — | Plasma treatment | Plasma treatment |
| Reactive functional group | — | Carboxy group Hydroxyl group | Carboxy group Hydroxyl group |
| Hydrophilic polymer | PVP | PVP | PVP |
| Polyisocyanate | MDI | MDI | MDI |
| Step of forming lubricating coated film | Mixed coating of hydrophilic polymer and polyisocyanate | Coating of polyisocyanate and hydrophilic polymer in this order (sequential coating) | Coating of polyisocyanate and hydrophilic polymer in this order (sequential coating) |
| Slipperiness at time of wetting | Impossible to perform evaluation due to film peeling | C | D |
| Durability at time of wetting | | D | D |

<Notes in Table>
PVP: polyvinylpyrrolidone
ACRIT 8BS-9000 has at least the following structural unit.

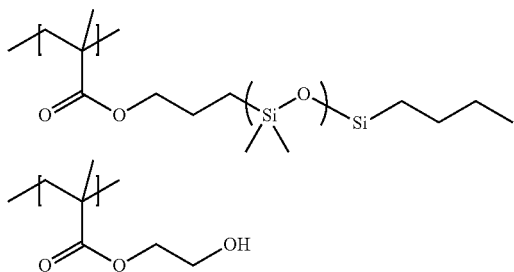

As shown in Table 1, since the sheet of Comparative Example 1 did not contain a reactive functional group, a lubricating coated film was not able to be formed even in a case where silicone rubber was used as the base material.

Further, in the sheet of Comparative Example 2, polyurethane was used as the base material without using silicone rubber. Further, a layer of polyisocyanate was formed on the sheet of Comparative Example 2, and a layer of a hydrophilic polymer was formed on the layer of this polyisocyanate. In other words, the sheet of Comparative Example 2 did not have the lubricating coated film (composition film) defined in the present invention, but had multiple layers formed of the layer of polyisocyanate and the layer of a hydrophilic polymer. Therefore, the slipperiness at the time of wetting and the durability at the time of wetting were in an unacceptable level. Further, the sheet of Comparative Example 3 did not have the lubricating coated film defined in the present invention similar to the sheet of Comparative Example 2 even in a case where silicone rubber was used as the base material. Therefore, the slipperiness at the time of wetting and the durability at the time of wetting were in an unacceptable level. On the contrary, in each sheet having the silicone base material containing a reactive functional group and the lubricating coated film defined in the present invention on the adhesive layer, both of the slipperiness at the time of wetting and the durability at the time of wetting were excellent.

Hereinbefore, the present invention has been described based on the embodiments thereof, but is not intended to be limited to any detailed description unless otherwise specified. The present invention should be broadly interpreted without departing from the spirit and the scope of the invention as set forth in the appended claims.

EXPLANATION OF REFERENCES 10, 20: medical lubricating member
a: silicone base material
b: lubricating coated film
c: adhesive layer

What is claimed is:

1. A medical lubricating member comprising:
   a tubular silicone base material;
   an adhesive layer which is provided coextensively on at least one surface of the tubular silicone base material; and
   a lubricating coating which is formed on a surface of the adhesive layer opposite to a surface where the tubular silicone base material is in contact,
   wherein the adhesive layer is a layer of a polymer having a polysiloxane structure,
   the polymer having a polysiloxane structure has a structural unit represented by Formula (1) below and at least one of a structural unit represented by Formula (2) below, a structural unit represented by Formula (3) below, and a structural unit represented by Formula (4) below,
   the lubricating coating bonds with a reactive functional group contained in the surface of the adhesive layer, and
   the lubricating coating is formed of a composition containing a hydrophilic polymer and polyisocyanate, Formula (1)

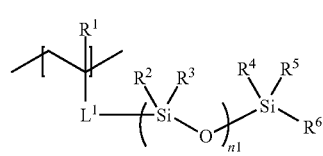

wherein $R^1$ to $R^6$ represent a hydrogen atom or an organic group, $L^1$ represents a single bond or a divalent linking group, and n1 is an integer of 3 to 10000,

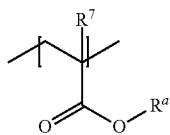

Formula (2)

wherein $R^7$ and $R^a$ represent a hydrogen atom or an organic group,

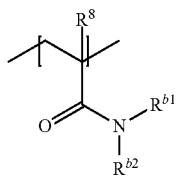

Formula (3)

wherein $R^8$, $R^{b1}$, and $R^{b2}$ represent a hydrogen atom or an organic group, and

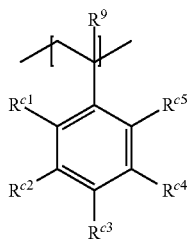

Formula (4)

wherein $R^9$ represents a hydrogen atom or an organic group, and $R^{c1}$ to $R^{c5}$ represent a hydrogen atom, a halogen atom, or an organic group.

2. The medical lubricating member according to claim 1, wherein the lubricating coating is provided at least inside the tubular silicone base material.

3. The medical lubricating member according to claim 1, wherein the reactive functional group is at least one of an amino group, an isocyanato group, a glycidyl group, a hydroxyl group, a carboxy group, a formyl group, an acid anhydride group, or an oxazoline ring.

4. The medical lubricating member according to claim 1, wherein the hydrophilic polymer is at least one of a hydrophilic polysaccharide and a hydrophilic vinyl polymer.

5. The medical lubricating member according to claim 4, wherein the hydrophilic polymer is at least one of hyaluronic acid, chondroitin sulfate, alginic acid, carrageenan, agarose, methyl cellulose, carboxymethyl cellulose, hydroxypropyl methyl cellulose, oxidized cellulose, polyvinylpyrrolidone, a maleic acid anhydride copolymer, polyacrylic acid, poly-N-vinylacetamide, an acrylamide copolymer, poly(2-(methacryloyloxy)ethylphosphoryl choline), N-(3-sulfopropyl)-N-(methacryloxyethyl)-N,N-dimethylammonium betaine, and N-methacryloyloxyethyl-N,N-dimethylammonium-α-N-methylcarboxy betaine.

6. The medical lubricating member according to claim 5, wherein the hydrophilic polymer is at least one of polyvinylpyrrolidone, the maleic acid anhydride copolymer, or hyaluronic acid.

7. The medical lubricating member according to claim 1, wherein the polyisocyanate is at least one of an aliphatic polyisocyanate, an alicyclic polyisocyanate and an aromatic polyisocyanate.

8. The medical lubricating member according to claim 7, wherein the polyisocyanate is at least one of 1,6-hexamethylene diisocyanate, isophorone diisocyanate, 2,4-tolylene diisocyanate, 2,6-tolylene diisocyanate, m-xylylene diisocyanate, or 4,4'-diphenylmethane diisocyanate.

9. The medical lubricating member according to claim 1, wherein a mass ratio between a content of the hydrophilic polymer and a content of the polyisocyanate in the lubricating coating is 1:0.01 to 1:1.

10. The medical lubricating member according to claim 1, wherein the medical lubricating member is a member for a medical device selected from a balloon, a connector, a rubber component for a medical device, an angiography tube, a tracheal tube, a feeding tube, a tube for a urinary system, an endoscope overtube, and a catheter.

11. A medical device comprising the medical lubricating member according to claim 1 and is selected from a balloon, a connector, a rubber component for a medical device, an angiography tube, a tracheal tube, a feeding tube, a tube for a urinary system, an endoscope overtube, and a catheter.

12. A method of producing a medical lubricating member, comprising:
a step of coating an adhesive layer coextensively on a tubular silicone base material, the adhesive layer containing a reactive functional group in a surface thereof,
a step of coating the adhesive layer with a lubricating composition containing a hydrophilic polymer and polyisocyanate; and
a step of heating the composition at 100° C. or higher,
wherein the lubricating composition bonds with the reactive functional group,
wherein the adhesive layer is a layer of a polymer having a polysiloxane structure,
the polymer having a polysiloxane structure has a structural unit represented by Formula (1) below and at least one of a structural unit represented by Formula (2) below, a structural unit represented by Formula (3) below, and a structural unit represented by Formula (4) below,

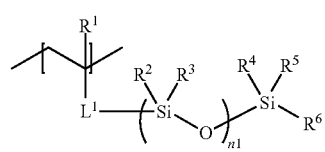

Formula (1)

wherein $R^1$ to $R^6$ represent a hydrogen atom or an organic group, $L^1$ represents a single bond or a divalent linking group, and n1 is an integer of 3 to 10000,

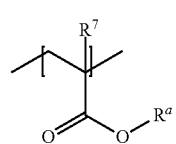

Formula (2)

wherein $R^7$ and $R^a$ represent a hydrogen atom or an organic group,

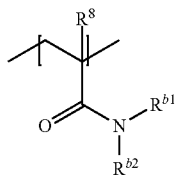

Formula (3)

wherein $R^8$, $R^{b1}$, and $R^{b2}$ represent a hydrogen atom or an organic group, and

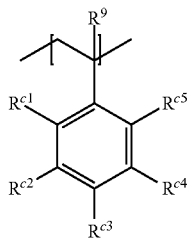

Formula (4)

wherein $R^9$ represents a hydrogen atom or an organic group, and $R^{c1}$ to $R^{c5}$ represent a hydrogen atom, a halogen atom, or an organic group.

13. The method of producing a medical lubricating member according to claim 12, wherein a mass ratio between a content of the hydrophilic polymer and a content of the polyisocyanate in the lubricating composition is 1:0.01 to 1:1 in terms of a mass ratio.

14. The method of producing a medical lubricating member according to claim 12, wherein the hydrophilic polymer is at least one of a hydrophilic polysaccharide and a hydrophilic vinyl polymer.

15. The method of producing a medical lubricating member according to claim 14, wherein the hydrophilic polymer is at least one of hyaluronic acid, chondroitin sulfate, alginic acid, carrageenan, agarose, methyl cellulose, carboxymethyl cellulose, hydroxypropyl methyl cellulose, oxidized cellulose, polyvinylpyrrolidone, a maleic acid anhydride copolymer, polyacrylic acid, poly-N-vinylacetamide, an acrylamide copolymer, poly(2-(methacryloyloxy)ethylphosphoryl choline), N-(3-sulfopropyl)-N-(methacryloxyethyl)-N,N-dimethylammonium betaine, and N-methacryloyloxyethyl-N,N-dimethylammonium-α-N-methylcarboxy betaine.

\* \* \* \* \*